(12) United States Patent
Iida et al.

(10) Patent No.: US 8,609,342 B2
(45) Date of Patent: Dec. 17, 2013

(54) REPORTER GENE ASSAY METHOD

(75) Inventors: Mitsuru Iida, Naruto (JP); Hideo Oguri, Tokushima (JP)

(73) Assignee: Otsuka Pharmaceutical Co., Ltd., Tokyo (JP)

( * ) Notice: Subject to any disclaimer, the term of this patent is extended or adjusted under 35 U.S.C. 154(b) by 1129 days.

(21) Appl. No.: 10/498,265

(22) PCT Filed: Dec. 13, 2002

(86) PCT No.: PCT/JP02/13050
§ 371 (c)(1),
(2), (4) Date: May 6, 2005

(87) PCT Pub. No.: WO03/054220
PCT Pub. Date: Jul. 3, 2003

(65) Prior Publication Data
US 2006/0166196 A1     Jul. 27, 2006

(30) Foreign Application Priority Data
Dec. 13, 2001     (JP) ................... 2001-379908

(51) Int. Cl.
*C12Q 1/68*     (2006.01)
*C12Q 1/66*     (2006.01)
*C12Q 1/02*     (2006.01)
*C12N 5/10*     (2006.01)

(52) U.S. Cl.
USPC ............. 435/6.13; 435/8; 435/29; 435/358

(58) Field of Classification Search
None
See application file for complete search history.

(56) References Cited

U.S. PATENT DOCUMENTS

| | | | |
|---|---|---|---|
| 5,728,534 A * | 3/1998 | Mendelsohn et al. | 435/7.1 |
| 6,025,192 A * | 2/2000 | Beach et al. | 506/14 |
| 6,117,639 A * | 9/2000 | Germann et al. | 435/6 |
| 2002/0058290 A1 * | 5/2002 | Ostrowski et al. | 435/7.21 |

FOREIGN PATENT DOCUMENTS

| | | |
|---|---|---|
| EP | 1045035 A2 | 10/2000 |
| WO | WO 99/11760 A | 3/1999 |

OTHER PUBLICATIONS

Zhang et al. (1996) Biochem. Biophys. Res. Commun. 227:707-711.*
Feinbaum (1998) "Vectors Derived from Plasmids: Introduction to Plasmid Biology" in Current Protocols in Molecular Biology, John Wiley & Sons, Inc., pp. 1.5.1-1.5.17.*
Balbin et al. (1996) J. Biol. Chem. 271:15175-15181.*
Bennett et al. Fusion of green fluorescent protein with the ZeocinTM-resistance marker allows visual screening and drug selection fo transfected eukaryotic cells. BioTechniques, vol. 24, No. 3, pp. 478-482, 1998.*
Hellweg et al. Enhanced green fluorescent protein as reporter protein for biomonitoring of cytoxic effects in mammalian cells. Analytica Chimica Acta, vol. 427, pp. 191-199, Jan. 2001.*
C.E. Hellweg, C. Baumstark-Khan, G. Horneck, Enhanced green fluorescent protein as reporter protein for biomonitoring of cytotoxic effects in mammalian cells, Analytica Chimica Acta, Jan. 2001, pp. 191-199, vol. 427, Germany.
Rudakoff, B. et al Dual Reporter Systems in Yeast and Mammalian Cells for Assessing Progesterone Receptor Modulators Journal of Cellular Biochemistry 73(1):126-136 1999.
Vinggaard, A.M. et al Rapid and Sensitive Reporter Gene Assays for Detection of Antiandrogenic and Estrogenic Effects of Environmental Chemicals Toxicology and Applied Pharmacology 155(2):150-160, 1999.
Data Medline, National Library of Medicine, PMID: 10421759 Sandman K.E., et al., Rapid fluorescence-based reporter-gene assays to evaluate the cytotoxicity and antitumor drug potential of platinum complexes, abstract, Chem. Biol. 1999, vol. 6, No. 8, pp. 541 to 551.
International Search Report of PCT/JP02/13050, mailed Feb. 18, 2003.

* cited by examiner

*Primary Examiner* — Jennifer Dunston
(74) *Attorney, Agent, or Firm* — Sughrue Mion, PLLC

(57) ABSTRACT

The invention provides a reporter gene assay method by which the sex hormone-like activity inherent in a test substance can be accurately assayed excluding the effects caused by a decrease in cell activity (protein expressing capacity). The assay method is a reporter gene assay method using luciferase-expressing cells which comprises further transferring a GFP gene into the luciferase-expressing cells, measuring the luciferase expression level and GFP expression level, and making a judgment about the thus-measured luciferase expression level using the decrease in GFP expression level as an indication of the decrease in cell activity.

10 Claims, 6 Drawing Sheets

REPORTER GENE ASSAY METHOD

TECHNICAL FIELD

The present invention relates to a reporter gene assay method.

This Application is a 371 of PCT/JP02/13050, filed Dec. 13, 2002; the disclosure of which is incorporated herein by reference.

BACKGROUND ART

In recent years, it has been reported that various substances having sex hormone-like activity occur in the environment, and the problem of environmental pollution by such substances has been becoming more and more serious. The substances having sex hormone-like activity are chemical substances acting as endocrine disruptors exerting an influence on biogenic hormones. Typical examples of such substances include substances affecting the functions of estrogen and androgen, namely sex hormone-like substances such as estrogen-like acting substances, antiestrogen-like acting substances, androgen-like acting substances and antiandrogen-like acting substances.

There is growing apprehension that such sex hormone-like substances will destroy the hormonal balance in animals and disturb the ecosystem or cause various diseases. Therefore, the advent of means for screening out in a simple and accurate manner such sex hormone-like substances from among the existing chemical substances and the chemical substances that will be newly developed in the future is now demanded in the relevant industries.

Currently known as the means for detecting sex hormone-like substances are the reporter gene assay methods which utilize an estrogen receptor gene or androgen receptor gene (cf. e.g. Japanese Unexamined Patent Publication Nos. 2000-300258 and 2000-300259). For the method utilizing the androgen receptor gene, for instance, the principle of the assay method is as follows.

Thus, when the androgen receptor (AR) gene-expressing cells with a reporter gene (e.g. luciferase (Luc) gene) introduced therein so that the expression of the reporter gene can be controlled by the transcriptional regulatory region having an androgen-response elements (ARE) (such cells are hereinafter sometimes referred to as "luciferase-expressing cell") are brought into contact with an androgen-like acting substance or antiandrogen-like acting substance as a test substance, this test substance binds to the AR gene occurring in the cell and activates the androgen receptor. As a result of this activation, the transcription of the reporter gene is initiated and the transcription product (reporter protein, e.g. Luc) is produced. Therefore, the expression of the AR gene can be estimated by taking the expression level or activity of this transcription product as an indication, hence the androgen-like activity or antiandrogen-like activity of the test substance can be estimated.

In cases where, in the assay method using the above luciferase-expressing cells is used, a substance having an antagonistic activity against the androgen receptor (antiandrogen activity) is used as the test substance and when a fixed amount of an agonist is added to the assay system in advance, the inhibitory activity of the test substance against that agonist can be evaluated in terms of the decrease in the expression level or activity of luciferase as a reporter protein.

However, since this assay system uses living cells, not only the antagonist activity intrinsic in the test substance but also a toxicity (e.g. cytotoxicity) of the test substance, for instance, presumably causes the decrease in reporter protein activity. That is to say, the substance to be tested is by nature toxic to cells and, as the concentration thereof increases, the cytotoxicity thereof increases, resulting in hypofunction of the cells themselves, hence in a reduced level of reporter protein expression. Therefore, this assay system has a fatal defect in that the cytotoxicity or like activity of the test substance counterbalances the antagonistic activity of the test substance, which is to be assayed, and thus makes it difficult to accurately detect and assay that activity. Similarly, when the test substance is a substance having an agonistic activity, the cytotoxicity or like activity of the test substance itself renders it difficult to accurately detect and assay the agonist activity desired to be known, in the same manner as mentioned above.

In the art, there is no means for precisely knowing the correlation between the sex hormone-like activity of such a test substance and such a factor as cytotoxicity that may lead to erroneous judgments of the detection results, and no means has been developed for properly evaluating test substances for sex hormone-like activity while neutralizing the effects of such factors. Thus, there is no indicator known in the art that can accurately reflect the cellular hypofunction (reduction in activity), in particular the reduction in cellular capacity for protein expression, due to the cytotoxicity or like activity of the test substance. Of course, there is no technology developed for assaying the sex hormone-like activity of a test substance utilizing such indicator.

Meanwhile, technologies of counting viable cells are known in the art [e.g. MTT method (cf. e.g. Molecular and Cellular Endocrinology, 160, (2000), pp. 39-49) and cell fluorescence labeling method using AlamarBlue (cf. e.g. Toxicology and Applied Pharmacology, 155, 150-160 (1999)). However, these technologies merely serve as means for judgment about life or death of cells. They can never make it possible to accurately assay and judge about such cellular hypofunction as mentioned above, in particular a reduced protein-expressing capacity. Even if these technologies are combined with the above-discussed reporter gene assay methods, it will be impossible to perform accurate sex hormone-like activity assaying by subtracting the cellular hypofunction-due errors from the values measured in the reporter gene assay systems.

An object of the present invention is to provide an improved bioassay method by which the sex hormone-like activity inherent in a test substance can be accurately assayed and judged by accurately estimating the test substance-due hypofunction of cells used in this type of reporter gene assay system, namely the variation in cellular protein expression activity.

DISCLOSURE OF THE INVENTION

As a result of intensive investigations, the inventors found that the above object can be achieved by an assay method and modifications thereof as specified below. The present invention was accomplished based on this finding.

The invention thus provides the following assay method and modifications/variations:

1. A reporter gene assay method using luciferase-expressing cells, comprising transferring a GFP gene into the luciferase-expressing cells, measuring the luciferase expression level and GFP expression level and making a judgment about the thus-measured luciferase expression level using the decrease in GFP expression level as an indication of the decrease in cell activity.

2. An assay method as set forth above under 1, wherein the luciferase-expressing cells are cells in which an estrogen receptor gene or androgen receptor gene can be expressed.

3. An assay method as set forth above under 1, wherein the luciferase-expressing cells are cells with an androgen receptor expression vector introduced therein.

4. An assay method as set forth above under 1, wherein the luciferase-expressing cells are cells with a luciferase gene expression plasmid introduced therein.

5. An assay method as set forth above under 1, wherein the luciferase-expressing cells are cells with an androgen receptor expression vector and a luciferase gene expression plasmid as introduced therein.

6. An assay method as set forth above under 1, wherein the luciferase-expressing cells are CHO cells serving as host cells.

7. An assay method as set forth above under any of 1 to 6, wherein the GFP gene transfer is effected by introduction of a GFP expression vector.

8. An assay method as set forth above under any of 1 to 6, wherein the GFP gene transfer is effected by introduction of an EGFP gene expression vector.

9. An assay method as set forth above under 1 which is an assay method intended for use in testing a sex hormone-like substance selected from among estrogen-like acting substances, antiestrogen-like acting substances, androgen-like acting substances and antiandrogen-like acting substances.

The present invention further provides cells for use in the reporter gene assay method specified above under 1, namely cells resulting from further transfer of a GFP gene into luciferase-expressing cells (hereinafter such cells are sometimes referred to as "cells of the invention").

Furthermore, the invention provides the use of such cells (cells of the invention) resulting from further transfer of a GFP gene into luciferase-expressing cells in the reporter gene assay method as set forth above under 1.

In this specification, "luciferase-expressing cells" indicate cells in which the gene for a receptor of a sex hormone such as, for example, estrogen or androgen can be expressed and in which a luciferase reporter gene is introduced under the control of a transcriptional regulatory region having a sequence of recognizing the receptor encoded by the receptor gene. Thus, those cells have the receptor gene inherently or as a foreign gene, and the reporter gene can be expressed under the control of the receptor gene.

The reporter gene assay method of the invention utilizes the very good correlation between the reduction in function of the cells utilized in this assay system as caused by the test substance (sex hormone-like substance) (reduction in protein expression capacity) and the level of GFP expression owing to the GFP gene transferred into the cells. According to the assay method of the invention, it is possible to properly evaluate the degree of cellular activity, namely the degree of retention of the inherent protein expression capacity of the cells, by measuring the GFP expression level. Therefore, in the reporter gene assay method according to the invention, the sex hormone-like activity of a test substance can be accurately assayed and evaluated while avoiding the risk of judging such activity erroneously as being due to a decrease in cellular activity.

In the following, the present invention is described in further detail.

Luciferase-Expressing Cells

As for the luciferase-expressing cells for preparing the cells of the invention for use in the method of the invention, those utilized in the conventional reporter gene assay methods can all be utilized (cf. e.g. Japanese Unexamined Patent Publication No. 2000-300258). More specifically, the cells may be ones resulting from transfer of a foreign gene for the expression of luciferase, if necessary together with a sex hormone receptor gene (which may further contain an appropriate DNA for the expression of the receptor gene) for the reporter gene assay, into conventional animal cells as host cells.

Utilizable as the host cells are, for example, human, mouse, rat or other mammal-derived cells, frog and other amphibian-derived cells, and insect-derived cells. In view of the operability and reproducibility, among others, the host cells are preferably cells capable of being subcultured stably. Specific examples of the preferred host cells are human-derived 293 cells, human-derived A-431 cells, human-derived HeLa cells, human-derived MCF7 cells, human-derived neuroblastoma cells, mouse-derived NIH3T3 cells, hamster-derived CHO-K1 cells, hamster-derived BHK-21 cells, monkey-derived COS-1 cells, monkey-derived CV-1 cells, rat-derived L6 cells, and mink-derived Mv 1 Lu cells, for instance. Among these cells, there are cells inherently having a receptor gene for reporter gene assay.

When the luciferase gene as a reporter gene and the GFP gene as an indicator of the change in cellular activity are transferred thereinto, such cells inherently having a receptor gene for reporter gene assay are converted to the cells of the invention, namely cells for use in the reporter gene assay according to the invention.

As for the cells inherently having no such receptor gene as mentioned above, for example HeLa cells, NIH3T3 cells or COS cells, an appropriate sex hormone receptor gene (further comprising an appropriate DNA for the expression thereof, for example a promoter sequence etc.), for example the androgen receptor gene, is transferred into them to provide them with the ability to express said gene.

A number of receptor genes for reporter gene assay are known in the art. Typical examples thereof are androgen receptor genes (cDNA genes) derived from the human androgen receptor gene (GenBank Accession No. M23263), rat androgen receptor gene (GenBank Accession No. M23264), mouse androgen receptor gene (GenBank Accession No. X59592), etc. Other typical examples of the receptor genes are estrogen receptor genes (cDNA genes), such as the human estrogen receptor α gene (GenBank Accession No. X03635), human estrogen receptor β gene (Biochem. Biophysical Res. Com., 243, 122-126 (1998)), rat estrogen receptor α gene (GenBank Accession No. U57439), and mouse estrogen receptor α gene (GenBank Accession No. M38651).

In transferring these receptor genes into host cells, these genes are inserted into a vector at a site downstream from an appropriate promoter in a functionally coupled form so that they can function within the cells, and the vectors obtained are each introduced into the cells. Such vector can be introduced into the cells and the cells can be thus provided with the capability to express the relevant gene by conventional processes well known in the art (cf. e.g. the above-cited Japanese Unexamined Patent Publication No. 2000-300258).

It is necessary that the cells for reporter gene assay should have a luciferase gene introduced therein as a reporter gene. The luciferase gene is transferred into the cells in the same manner as in the conventional reporter gene assays so that its expression can be controlled by the transcriptional regulatory region having a receptor recognition sequence. Such control can be established in the conventional manner (cf. e.g. the above-cited Japanese Unexamined Patent Publication No. 2000-300258). Specific examples of the luciferase gene as the reporter gene include the genes coding for firefly luciferase, *Renilla reniformis* (sea pansy) luciferase, etc.

As regards the androgen-response elements (ARE) as a typical example of the receptor recognition sequence, there may be mentioned, for example, the C(3) gene (Karvonen, U. et al., J. Biol. Chem., 272 (25), 15973-9 (1997)) etc.

Cells of the Invention with a GFP Gene Introduced Therein

The cells of the invention are prepared by further transferring a GFP gene into luciferase-expressing cells having an inherent or transferred receptor gene. The GFP gene to be transferred may be any of various GFP genes known in the art. Specific examples thereof are EGFP (enhanced GFP) and variants thereof, for example EYFP and ECFP (all being available from Clontech). These commercially available GFP genes have already been prepared in the form of DNAs suited for introduction into various cells, and can be readily transferred into cells according to the manuals attached to the respective products. The utilization of such GFP genes is also advantageous in that the phenomena occurring in living cells can be observed and measured directly in terms of fluorescent intensities without the necessity of using any cofactor or substrate. These GFP genes are further advantageous in that they are nontoxic to cells and can emit the desired fluorescence within a wide variety of cells.

In a specific preparation example of the cells of the invention, inclusive of the transfer of the above-described GFP gene, stable transformant cells can be obtained, for example, by transfecting CHO-K1 cells as the host cells with the vector pZeoSV2(−) (Invitrogen) capable of expressing an androgen receptor gene under the control of the SV40 promoter, the luciferase reporter gene expression plasmid pIND ARE-B10 resulting from insertion of an androgen-responsive element, a heat shock promoter and a luciferase gene, in that order, into the mammalian expression vector pIND/Hygro (Invitrogen) and the EGFP expression vector pcDNA-EGFP resulting from insertion of the EGFP gene (Clontech) into the mammalian expression vector pcDNA3.1Zeo(−) (Invitrogen). A detailed description of such procedure will appear later in the example section.

The cell culture medium, the cell culture conditions, the conditions of transfection with the respective vector plasmids and other conditions to be used in preparing the cells of the invention can all be the same as in the conventional methods utilizing host cells of that kind and gene transfer vectors of those kinds.

The cells of the invention can be prepared not only by the transfection technique utilizing such respective expression vectors (cyclic DNAs) as mentioned above but also by introduction of the respective genes in the form of linear DNAs by the general DNA introduction techniques, such as the electroporation, calcium phosphate, and lipofection techniques, so long as the receptor gene, luciferase reporter gene and GFP gene transferred can function in the cells. That the cells prepared function as desired can be confirmed by measuring, in the conventional manner, the level of expression of the luciferase gene introduced (luminescent intensity).

The cells of the invention obtained in the above manner can be utilized in detecting and assaying various test substances, for example sex hormone-like acting substances.

The Reporter Gene Assay Method of the Invention

Among typical examples of the test substances to which the reporter gene assay method utilizing the cells of the invention is applicable, there are chemical substances showing agonistic action against estrogen receptors (estrogen-like acting substances) and chemical substances showing antagonistic action against the same (antiestrogen-like acting substances). Other typical examples include chemical substances showing agonistic action against androgen receptors (androgen-like acting substances) and chemical substances showing antagonistic action against the same (antiandrogen-like acting substances).

The technique of the reporter gene assay method of the invention for identifying such test substances may be basically the same as in the reporter gene assay methods of this kind known in the art except that the cells of the invention are utilized.

Specifically, the cells of the invention are first sown in cell culture vessels. When a 96-well plate is used, for instance, the cells are sown generally in a proportion of about $10^3$ to $2\times10^4$ cells per well, and cultured for about 1 hour to overnight. Then, the test substance is added to the cell culture fluids. When the agonistic activity of the test substance is to be assayed, a solution prepared by dissolving the test substance in a solvent or the solvent alone is added to the cell culture fluids so that the final concentration of the solvent in the culture fluids may generally amount to about 0.1 to 2%. When the antagonistic activity of the test substance is to be assayed, a system is prepared by adding a solution prepared by dissolving an androgen receptor ligand, for example dihydrotestosterone (DHT), in a solvent to the culture fluids so that the ligand concentration therein may generally amount to about EC50 and, in parallel, a system is prepared by further adding the test substance to the above system. Here, dimethyl sulfoxide (DMSO), ethanol, and the like are often used as the solvent.

In the assay method of the invention, the cells prepared as mentioned above are cultured for 1 hour to about 72 hours, for instance, and the level of expression of the luciferase gene as the reporter gene and the GFP expression level are then measured. The GFP expression level measurement can be made by directly measuring the fluorescent intensity. This GFP expression level measurement is preferably carried out before, more preferably just prior to, the luciferase expression level measurement described below. The luciferase expression level measurement can be made, for example, by determining the level of luminescence due to the luciferase produced in the cell extract using luciferin, which is the substrate of luciferase.

When, in agonistic activity testing of a test substance, the luciferase activity per cell in the cell system containing the test substance added thereto is higher than in the cell system containing the solvent alone as added thereto, the test substance is judged to show agonistic activity against the androgen receptor. When, in antagonistic activity testing of a test substance, the luciferase activity in the cell system containing an androgen receptor-binding ligand and the test chemical substance added thereto is lower as compared with the luciferase activity in the cell system containing the ligand alone as added thereto, the test substance is judged to have androgen receptor antagonist activity.

In making the above-mentioned judgments and evaluations, however, the cytotoxicity and/or the reduction in the protein expressing function (reduction in activity) of the cells used as shown or caused by the test substance, for instance, is not taken into consideration. When the cytotoxicity and the reduction in cellular activity shown or caused by the test substance, among others, are taken into consideration, cases may arise where even when the test substance is judged to have antagonistic activity (to be a substance reducing the luciferase activity) according to the above criteria, the decrease in luciferase activity is actually caused by a decrease in cellular function (reduced protein expression capacity), hence the test substance really has no antagonistic activity.

The assay method of the invention, according to which the GFP expression level is measured together with the luciferase expression level, can avoid such erroneous misunderstanding of measurement results without fail. Namely, the decrease in GFP expression level as obtained according to the assay method of the invention accurately reflects the decrease in cellular activity (decrease in protein expression capacity), as is evident from the results shown later herein in the example section. Therefore, by using this GFP expression level as an indication, it becomes possible to judge as to whether the change in luciferase expression level is due to a decrease in cellular activity or not and, accordingly, it becomes possible to accurately evaluate the test substance for its actual antagonistic or like activity while excluding the measurement error arising from its cytotoxicity, for instance.

EFFECTS OF THE INVENTION

As described hereinabove, various chemical substances can be accurately identified as androgen receptor agonists or antagonists, for instance, according to the assay method of the invention which uses the cells of the invention. This identification can be utilized in detecting various endocrine disrupting substances, among others, and can further be utilized in searching for drug candidate compounds the targets of which are various receptors such as androgen receptors.

The cells of the invention can be frozen stored and, where needed, can be thawed and used. In this respect as well, they are suited for use in the above-mentioned field of application.

BEST MODES FOR CARRYING OUT THE INVENTION

The following examples illustrate the present invention in further detail. They are, however, by no means limitative of the scope of the invention.

Example 1

(1) Construction of an Androgen Receptor Expression Vector

The androgen receptor (AR) gene was amplified from human prostate total RNA by the RT-PCR technique, and the amplification product was subcloned into the cloning vector TA cloning (Invitrogen) and the base sequence thereof was determined. It was confirmed that this is identical with that of the human AR gene registered in GenBank.

The above DNA was cloned, as an insert DNA, in the SV40 promoter-containing expression vector pZeoSV2(−) (Invitrogen) at the BamHI site thereof. An AR expression vector, pZeoSV2-AR (total length: 3515 bps), was thus constructed.

Figure 1:
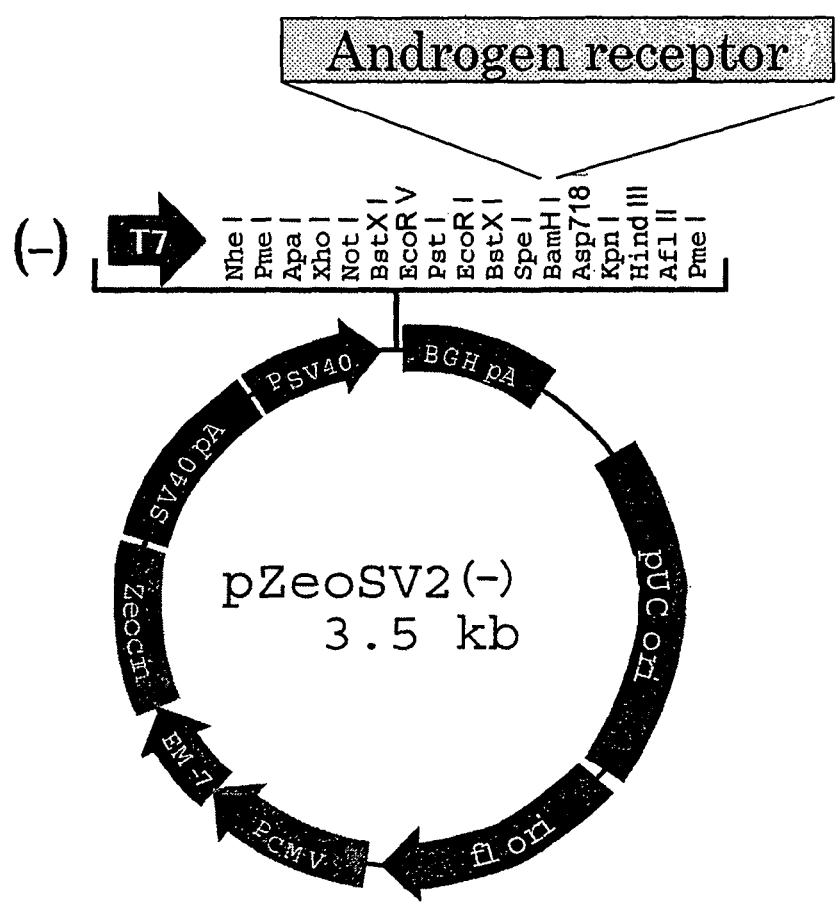
FIG. 1 is a schematic representation of typical characteristic features of an androgen receptor expression vector.

Typical characteristic features of this AR expression vector are shown in FIG. 1. The abbreviations used in FIG. 1 are as follows:
Psv40: SV40 promoter
T7: T7 promoter/primer
BGH pA: BGH reverse priming site
pUC ori: pUC origin
PCMV: CMV promoter
f1 ori: f1 origin
PCMV: CMV promoter
EM-7: EM-7 promoter
Zeocin: Zeocin™ resistance gene
SV40pA: SV40 poly(A)

(2) Construction of a Luciferase Reporter Gene

Using the mammalian cell expression vector pIND/Hygro (Invitrogen), four androgen responsive elements (ARE, C(3) gene (Karvonen U., et al., J. Biol. Chem., 272 (25), 15973-9 (1997)) were introduced thereinto at a site upstream of the heat shock promoter (hs) in the same directionality, and the luciferase gene (Promega) was cloned therein at a site downstream from hs. Thus was constructed a luciferase reporter gene-containing plasmid, pIND ARE-B10 (total length: 6.9 kb).

Figure 2:
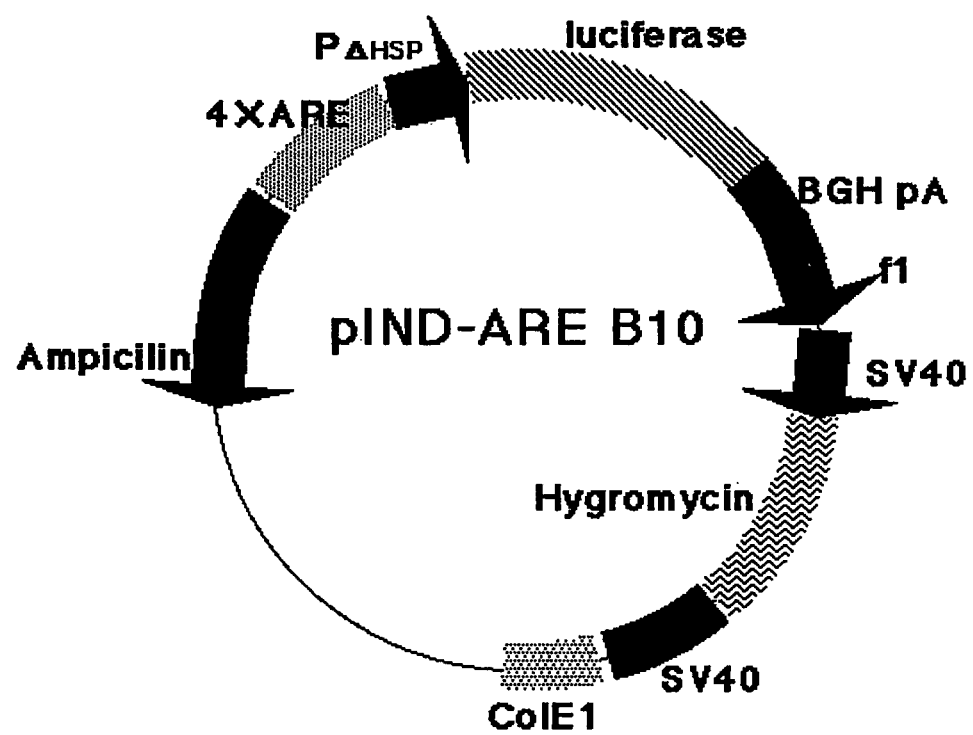
FIG. 2 is a schematic representation of typical characteristic features of a luciferase reporter gene vector.

Typical characteristic features of the plasmid obtained are shown in FIG. 2. The abbreviations used in FIG. 2 are as follows:
Ampicillin: Ampicillin resistance gene
4×ARE: Four repetitions of the ARE sequence
PΔHSP: Heat shock promoter (Invitrogen)
luciferase: Luciferase gene
BGHpA: BGH poly(A) (including the BGH reverse priming site)
f1: f1 origin
SV40: SV40 poly(A)
Hygromycin: Hygromycin resistance gene
Col E1: origin (3) Construction of an EGFP Expression Vector An EGFP expression vector, pcDNA-EGFP (total length: 5.7 kb) was constructed by cloning the EGFP gene (Clontech) into the mammalian cell expression vector pcDNA3.1Zeo(−) (Invitrogen) at the NheI-PmeI site thereof.

Figure 3:
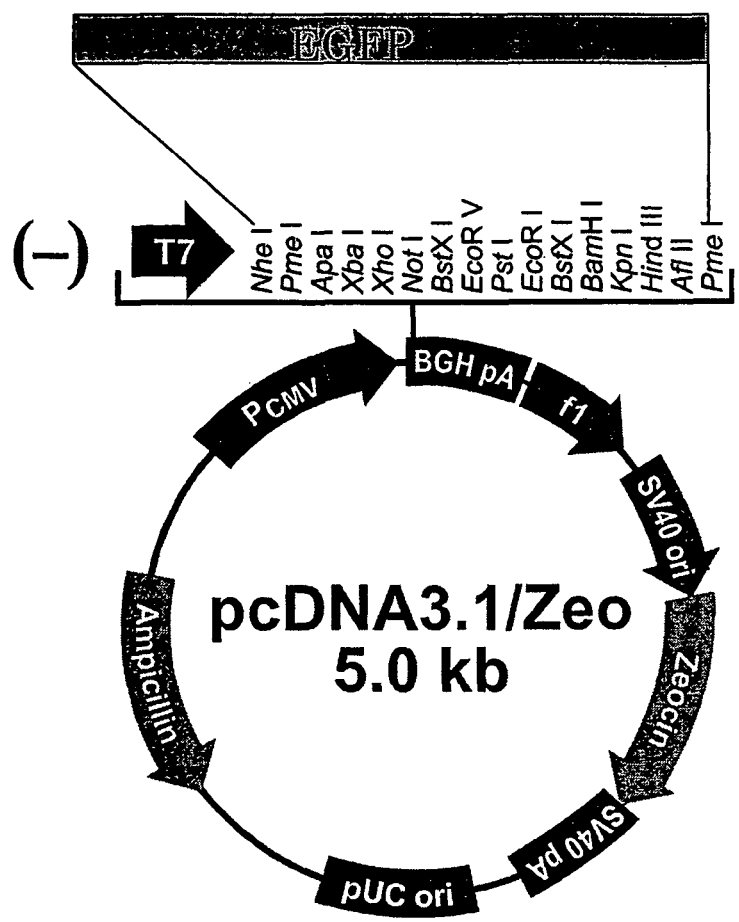
FIG. 3 is a schematic representation of typical characteristic features of an EGFP expression vector.

Typical characteristic features of the vector obtained are shown in FIG. 3. Typical characteristics of the vector shown in FIG. 3 and the abbreviations used in FIG. 3 are as follows:
pCMV: CMV promoter
T7: T7 promoter/primer site
BGH pA: BGH reverse priming site
f1: f1 origin
SV40 ori: SV40 promoter and origin
Zeocin: Zeocin™ resistance gene
SV40 pA: SV40 polyadenylation
pUC ori: pUC origin
Ampicillin: Ampicillin resistance gene (4) Production of Cells for the Reporter Gene Assay of the Invention CHO-K1 cells (cells deposited with ATCC) were developed on a 96-well plate (8000 cells/well). On the next day, transfection was carried in each well with 50 ng/well of pGL3-Control (retaining the SV40 promoter and containing the luciferase gene; Promega) and 4 ng/well of pcDNA-EGFP using 0.15 µL of FuGENE6™ (Roche) (at room temperature).

Thus were prepared cells for the reporter gene assay of the invention.

(5) The Reporter Gene Assay Method of the Invention (5-1) Assaying in the Presence of DMSO (without Adding any Test Substance)

To each well of the cells of the invention as prepared as described above under (4), 3 hours after transfection, DMSO was added to a final concentration of 0.125, 0.25, 1, 2, 4 or 10%.

After 24 hours following the addition of DMSO, the fluorescence intensity of EGFP expressed in each well was measured using Berthord's measuring apparatus ARVO. Immediately thereafter, the luciferase activity was measured using Steady-Glo™ (Promega) as a substrate and using Berthord's measuring apparatus ARVO.

For comparison, the following MTT assay and AlamarBlue assay were carried out using the respective assay kits. Thus, CHO-K1 cells with pGL3-Control alone introduced therein were used in lieu of the above-prepared cells, DMSO was added to each well to the same concentration as mentioned above and, after 24 hours of culture, the MTT assay was carried out. The MTT measurement was performed as indicated in the manual attached to the product.

Further, ALAMAR BLUE™ (Serotec) was added, to a concentration of 10% (w/v), to the CHO-K1 cell suspension cultured in each well in the presence of the same predetermined concentration of DMSO as mentioned above and, after 3-4 hours of incubation in an incubator at 37° C., the AlamarBlue assay was carried out using Berthord's measuring apparatus ARVO. The AlamarBlue measurement was performed as instructed in the manual attached to the product.

Figure 4:
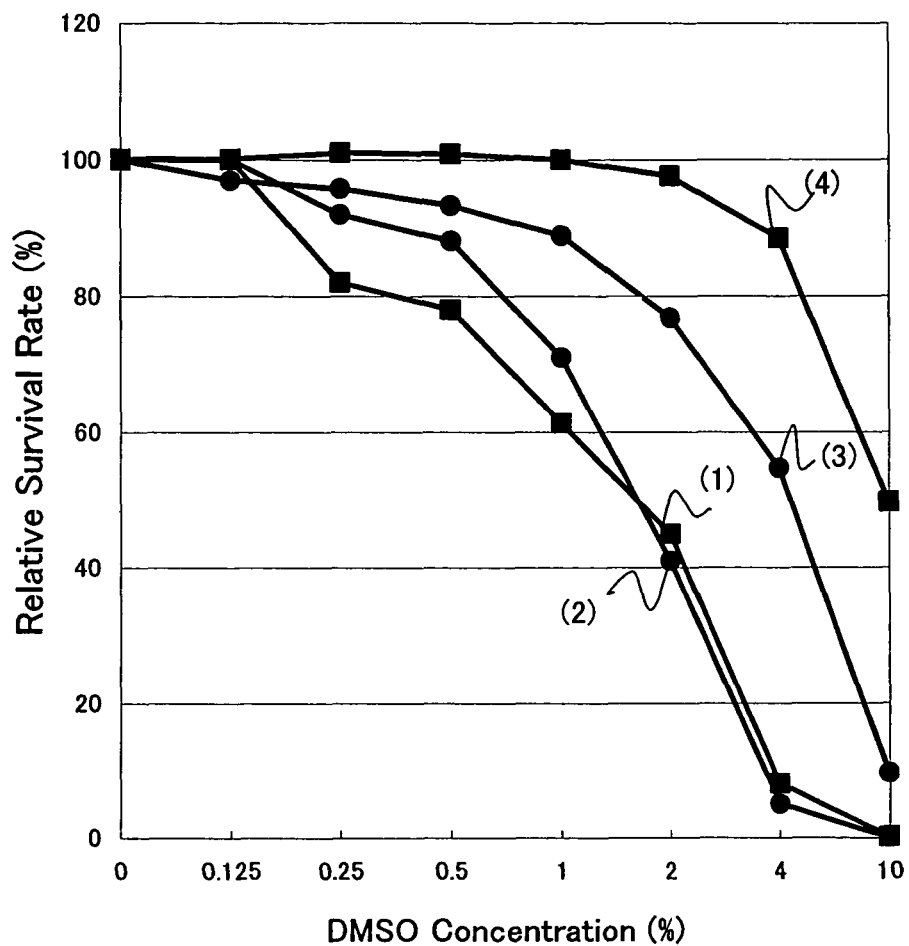
FIG. 4 is a graphic representation of the results of a relative surviving activity examination of cells by the assay method of the invention using DMSO as a test substance.

The results obtained are shown in FIG. 4.

In FIG. 4, the ordinate denotes the relative survival rate (%) (the relative measurement result value at each DMSO concentration with the measurement result in each test carried out without addition of DMSO being taken as 100), and the abscissa denotes the DMSO concentration (%). In the figure, graph (1) shows the luciferase activity measurement results, graph (2) shows the EGFP activity measurement results, graph (3) shows the AlamarBlue measurement results, and graph (4) shows the MTT activity measurement results.

The results shown in FIG. 4 indicate the following.

Thus, it is evident that the decreases in luciferase activity (cf. graph 1) as obtained by utilizing DMSO (generally used as a solvent for dissolving test substances) as the test substance, which is known to show no sex hormone activity, in the reporter gene assay using the cells of the invention are not due to the sex hormone activity which is the intended target of this assay system. Presumably, this is due to the cytotoxicity (cellular activity- or protein expression capacity-reducing activity) of DMSO to the test cells.

Meanwhile, this cytotoxicity can be determined by EGFP activity measurements (cf. graph 2).

The results shown in FIG. 4 indicate that the decreases in luciferase activity (graph 1) are in very good agreement with the decreases in EGFP activity (graph 2). From this, it can be concluded that the EGFP activity measurement sharply reflects the cytotoxicity (degree of cellular activity) in this assay system, hence is very effective in evaluating influential factors decreasing the protein expression capacity of cells.

On the contrary, the results (graphs 3 and 4) of the MTT activity and AlamarBlue activity measurements, which are known in the art to be useful in cytotoxicity evaluation, do not correspond to the decreases in luciferase activity (graph 1). While decreases in luciferase activity are observed from at the DMSO concentration of about 0.25%, a decrease in MTT activity, for instance, is first observed at a DMSO concentration of about 4% or above. If the cytotoxicity evaluated by such method is used as an indication, a test substance-due cytotoxic concentration range will arise within which the cytotoxicity cannot be evaluated in spite of its being actually exhibited and within which the decrease in luciferase activity will apprehensively be detected as a sex hormone activity.

(5-2) the Reporter Gene Assay Method of the Invention for Androgen Receptor Antagonist Detection The following four substances were used as the test substances.

(A) Cyproterone acetate (antiandrogen drug)
(B) Hydramethylnone (pesticide)
(C) CNP (pesticide)
(D) Progesterone (steroid hormone)

First, each test substance is dissolved in DMSO to a concentration of $10^{-3}$ M, and the solution was 10-fold diluted stepwise (serial dilution) to give diluted test sample solutions having a test substance concentration of $10^{-3}$ M to $10^{-9}$ M.

Then, each diluted sample solution was 100-fold diluted using a solution prepared by adding $5\times10^{-9}$ M) of 5α-dehydrotestosterone to DEMEM/F-12 medium (Gibco) (the test substance concentration becoming $10^{-5}$ M to $10^{-11}$ M).

CHO-K1 cells were developed on a 96-well plate to a size of about 8000 cells/84 μL of medium per well.

Separately, a solution for transfection was prepared by diluting 1 ng of pZeoSV-2-AR (prepared above in (1)), 50 ng of pIND ARE-B10 (prepared above in (2)) and 4 ng of pcDNA-EGFP (prepared above in (3)) with 6.25 μL of DMEM/F-12 medium and adding 0.15 μL of FuGENE6™ (Roche) to the dilution.

On the day after the above development, 6 μL/well of the solution for transfection was added to each well for transfection of the cells in each well (the cell culture fluid volume in each well being about 90 μL). Three hours later, each of serial 10-fold dilutions of each test sample (generally $10^{-5}$ M to $10^{-11}$ M) as prepared using the above-prepared medium (DMEM/F-12) supplemented with $5\times10^{-9}$ M of 5a-dehydrotestosterone was added in 10 μL portions, and cultivation was continued at room temperature (the final test substance concentrations: $10^{-6}$ M to $10^{-12}$ M).

At 24 hours after addition of the serial dilutions of the test sample, the GFP fluorescence intensity in each well was measured at the excitation wavelength of 485 nm and fluorescence wavelength of 535 nm using Berthord's ARVO.

After fluorescence intensity measurement, 100 μL of a luciferin solution (Steady-Glo™; Promega) was added to each well, and the luciferase-induced activity was measured in terms of luminescence intensity using a 96-well luminescence reader (Berthord's ARVO).

Figure 5:
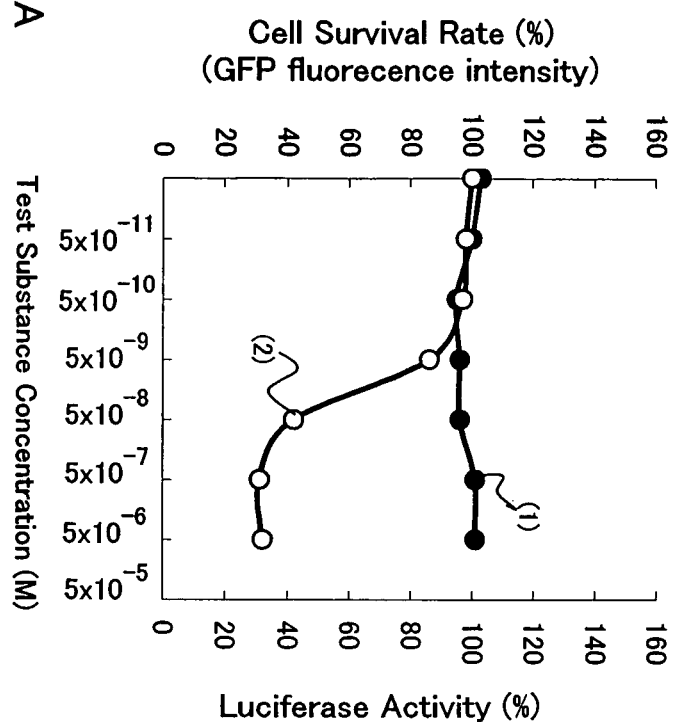
FIG. 5 (Panels A and B) is a graphic representation of the results of assaying of various test substances according to the assay method of the invention.
Figure 5:
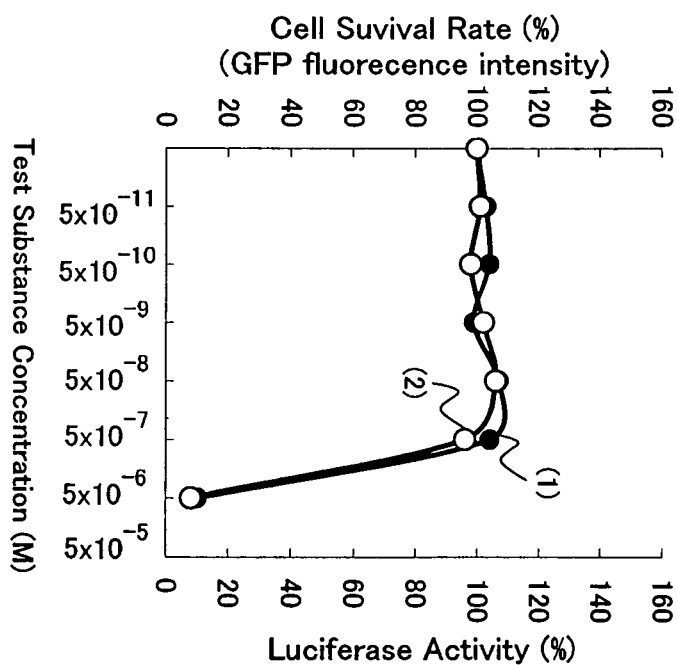
Figure 6:
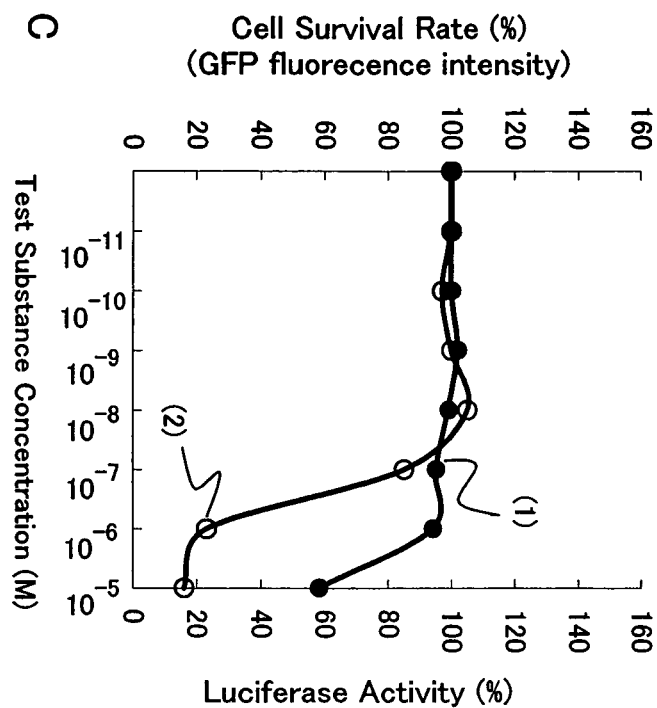
FIG. 6 (Panels C and D) is a graphic representation of the results of assaying of various test substances according to the assay method of the invention.
Figure 6:
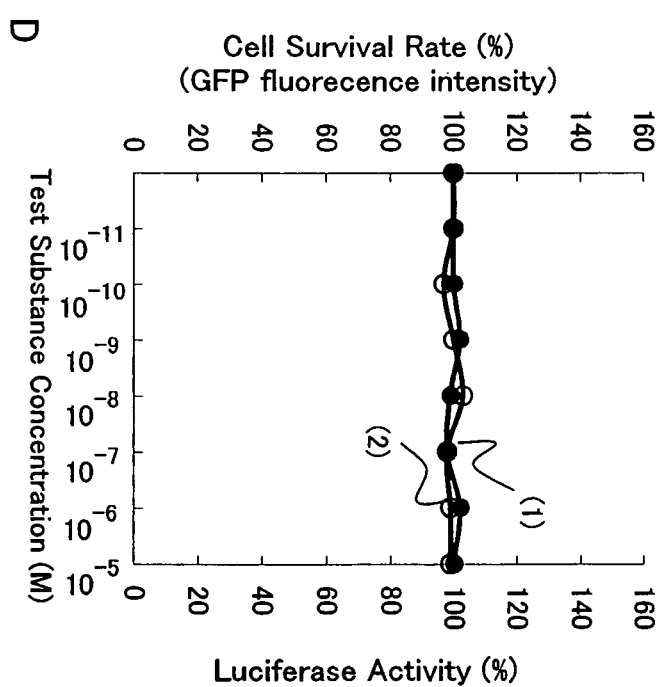

The results obtained are shown in FIGS. 5(A and B) and FIGS. 6(C and D). In FIGS. 5 and 6, the ordinate denotes the cell survival rate (%) (the relative EGFP fluorescence intensity value at each test substance concentration as determined by taking the EGFP fluorescence intensity value measured without addition of the test substance as 100; shown by curve (1)) as well as the luciferase activity percentage (shown by curve (2)). The abscissa denotes the test substance concentration (M).

The results shown in FIG. 5 and FIG. 6 indicate the following.

When progesterone, which neither binds to androgen receptors nor shows cytotoxicity, was used as the test substance (FIG. 6-D), the EGFP activity and luciferase activity each remained constant at the same level as the result obtained at a test substance concentration of 0 (zero).

As shown in FIG. 5-A, when cyproterone acetate, an agent known as an androgen receptor antagonist, was used as the test substance, the EGFP activity remained almost 100% until the test substance concentration of $5\times10^{-5}$ M and, within this concentration range, no cytotoxic effect was observed. Therefore, it follows that the decreases in luciferase activity within this concentration range were due to the antagonistic activity of the test substance against the androgen receptor.

In the case shown in FIG. 5-B where the agrochemical hydramethylnone was used as the test substance, it is understood that the decreases in luciferase activity were due to cytotoxicity, as evidenced by the decreases in EGFP activity. Therefore, this test substance is judged to have no antagonistic activity.

FIG. 6-C shows the results of the assay of the invention for the agrochemical CNP (chloronirophen) used as the test substance. Until the test substance concentration of $10^{-6}$ M, the EGFP activity remained at a level close to 100%. Thus, it can be judged that any cytotoxic effect will not manifest itself within this concentration range. Therefore, the decreases in luciferase activity within this concentration range indicate that the test substance has an antagonistic activity against the androgen receptor. However, since the EGFP activity markedly decreases at concentrations exceeding $10^{-5}$ M, it can be judged that a cytotoxic effect should contribute to the decreases in luciferase activity.

INDUSTRIAL APPLICABILITY

The present invention provides an improved bioassay method by which the sex hormone-like activity inherent in a test substance can be accurately assayed and judged by accurately estimating the hypofunction of cells due to the test substance used in the reporter gene assay system, namely the variation in cellular protein expression activity, and the assay system is useful in identifying various substances having sex hormone-like activity.

The invention claimed is:
1. A cell comprising
  (i) a polynucleotide sequence encoding luciferase, wherein said polynucleotide sequence is functionally linked to a first transcriptional regulatory sequence having a polynucleotide sequence recognizing a sex-hormone receptor,
  (ii) a polynucleotide sequence encoding GFP, wherein said polynucleotide sequence encoding GFP is functionally linked to a second transcriptional regulatory sequence, wherein the second transcriptional regulatory sequence is different from said first transcriptional regulatory sequence and does not have a polynucleotide sequence recognizing a sex-hormone receptor, and
  (iii) a polynucleotide sequence encoding the sex-hormone receptor,
  wherein the cell is a CHO cell,
  wherein the polynucleotide of (iii) is in a sex-hormone receptor expression vector comprising a drug resistance gene and a polynucleotide encoding the sex-hormone receptor, wherein the polynucleotide of (ii) is in a GFP expression vector comprising a drug resistance gene and a polynucleotide encoding GFP, and the polynucleotide of (i) is in a luciferase expression vector comprising a drug resistance gene and a polynucleotide encoding luciferase, and
  wherein the first transcriptional regulatory sequence has a polynucleotide sequence encoding a heat shock promoter, and the second transcriptional regulatory sequence has a polynucleotide sequence encoding a CMV promoter.
2. A reporter gene assay method, comprising:
  (a) contacting a cell which expresses luciferase with a test substance, wherein said cell comprises
    (i) a polynucleotide sequence encoding luciferase, wherein said polynucleotide sequence is functionally linked to a first transcriptional regulatory sequence having a polynucleotide sequence recognizing a sex-hormone receptor,
    (ii) a polynucleotide sequence encoding GFP, wherein said polynucleotide sequence encoding GFP is functionally linked to a second transcriptional regulatory sequence, wherein the second transcriptional regulatory sequence is different from said first transcriptional regulatory sequence and does not have a polynucleotide sequence recognizing a sex-hormone receptor, and
    (iii) a polynucleotide sequence encoding the sex-hormone receptor;
  (b) measuring the level of luciferase expression and the level of GFP expression in the cell contacted with a test substance in step (a); and thereafter
  (c) comparing the level of luciferase expression to the level of GFP expression so as to determine the antagonistic activity of the test substance against the sex-hormone receptor,
  wherein the cell is a CHO cell,
  wherein the polynucleotide of (iii) is in a sex-hormone receptor expression vector comprising a drug resistance gene and a polynucleotide encoding the sex-hormone receptor, wherein the polynucleotide of (ii) is in a GFP expression vector comprising a drug resistance gene and a polynucleotide encoding GFP, and the polynucleotide of (i) is in a luciferase expression vector comprising a drug resistance gene and a polynucleotide encoding luciferase, and
  wherein the first transcriptional regulatory sequence has a polynucleotide sequence encoding a heat shock promoter, and the second transcriptional regulatory sequence has a polynucleotide sequence encoding a CMV promoter.
3. The assay method as defined in claim 2, wherein the sex-hormone receptor is an estrogen receptor or an androgen receptor.
4. The assay method as defined in claim 2, wherein the cell comprises a polynucleotide sequence encoding a SV40 promoter functionally linked to the polynucleotide of (iii).
5. The assay method as defined in claim 2, wherein the drug resistance gene in the sex-hormone receptor expression vector is a zeocin resistance gene.
6. The assay method as defined in claim 2, wherein the drug resistance gene in the luciferase expression vector is a hygromycin resistance gene.
7. The assay method as defined in claim 2, wherein the drug resistance gene in said GFP expression vector is a zeocin resistance gene.
8. The assay method as defined in claim 4, wherein the SV40 promoter is linked to a drug resistance gene located upstream of the SV40 promoter.
9. The assay method as defined in claim 2, wherein the polynucleotide encoding a sex-hormone receptor is a polynucleotide sequence encoding an androgen receptor and the polynucleotide of (iii) is in an androgen receptor expression vector comprising a drug resistance gene and a polynucleotide sequence encoding an androgen receptor.
10. The assay method as defined in claim 2, wherein the polynucleotide of (ii) is a polynucleotide sequence encoding an EGFP and the polynucleotide of (ii) is in an EGFP expression vector comprising a drug resistance gene and a polynucleotide sequence encoding EGFP.

* * * * *